United States Patent
Stover et al.

(10) Patent No.: US 9,622,677 B1
(45) Date of Patent: *Apr. 18, 2017

(54) BRAIN IMPLANT DEVICE

(71) Applicant: THE ALFRED E. MANN FOUNDATION FOR SCIENTIFIC RESEARCH, Santa Clarita, CA (US)

(72) Inventors: Howard H. Stover, Los Angeles, CA (US); John C. Gord, Venice, CA (US); Charles L. Byers, Canyon Country, CA (US); Joseph H. Schulman, Santa Clarita, CA (US); Guangqiang Jiang, Irvine, CA (US); Ross Davis, Melbourne Beach, FL (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/476,682

(22) Filed: Sep. 3, 2014

Related U.S. Application Data

(60) Division of application No. 11/983,674, filed on Nov. 9, 2007, now Pat. No. 8,862,235, which is a continuation-in-part of application No. 11/173,863, filed on Jul. 1, 2005, now abandoned.

(60) Provisional application No. 60/857,890, filed on Nov. 9, 2006, provisional application No. 60/586,368, filed on Jul. 7, 2004.

(51) Int. Cl.
*A61B 5/0478* (2006.01)
*A61B 5/00* (2006.01)
*A61B 5/04* (2006.01)

(52) U.S. Cl.
CPC .......... *A61B 5/0478* (2013.01); *A61B 5/0006* (2013.01); *A61B 5/04012* (2013.01); *A61B 5/686* (2013.01)

(58) Field of Classification Search
CPC .............. A61N 1/3605; A61N 1/36082; A61N 1/36003; A61N 1/36; A61N 1/36014
USPC ...................................................... 607/45, 48
See application file for complete search history.

(56) References Cited

U.S. PATENT DOCUMENTS

| | | | | |
|---|---|---|---|---|
| 3,724,467 A | * | 4/1973 | Avery et al. | 607/117 |
| 3,821,949 A | * | 7/1974 | Hartzell | A61B 5/0482 |
| | | | | 600/545 |
| 5,816,247 A | * | 10/1998 | Maynard | A61B 5/048 |
| | | | | 600/544 |

(Continued)

*Primary Examiner* — Christopher D Koharski
*Assistant Examiner* — Roland Dinga
(74) *Attorney, Agent, or Firm* — Lewis Roca Rothgerber Christie LLP

(57) ABSTRACT

A brain implant device includes a housing containing communication and control electronics coupled to a conduit configured for monitoring signals from a brain's motor cortex and providing stimulation signals to the brain's sensory cortex. The brain implant device is capable of wireless communication with an external communication and control signal source by means of an antenna provided in the housing. The conduit is flexible and may contain upwards of 128 electrical conductors providing electrical connections between the device electronics and related sites on the motor and/or sensory cortex by means of a plurality of electrically conductive protuberances extending from the conduit and adapted for contact with such sites.

29 Claims, 17 Drawing Sheets

(56) References Cited

U.S. PATENT DOCUMENTS

| | | | |
|---|---|---|---|
| 6,647,296 B2* | 11/2003 | Fischell | A61N 1/3605 600/544 |
| 2003/0004428 A1* | 1/2003 | Pless | A61B 5/04012 600/544 |
| 2004/0176818 A1* | 9/2004 | Wahlstrand et al. | 607/45 |
| 2004/0249422 A1* | 12/2004 | Gliner | A61N 1/36167 607/58 |
| 2005/0010262 A1* | 1/2005 | Rezai | A61N 1/36071 607/46 |
| 2005/0245989 A1* | 11/2005 | Davis | A61N 1/36021 607/46 |

\* cited by examiner

BRAIN IMPLANT DEVICE

This application is a divisional of allowed U.S. application Ser. No. 11/983,674 filed on Nov. 9, 2007; which claims the benefit under 35 USC 119(e) of U.S. provisional application 60/857,890, filed on Nov. 9, 2006. U.S. patent application Ser. No. 11/983,674 filed on Nov. 9, 2007, is a continuation in part of U.S. patent application Ser. No. 11/173,863, filed Jul. 1, 2005, which claims the benefit under 35 USC 119(e) of U.S. provisional application 60/586,368, filed on Jul. 7, 2004.

THE FIELD OF THE INVENTION

The present invention is generally directed to implantable medical devices and in particular to a brain implant device in electrical communication with the brain's motor cortex and sensory cortex and in wireless communication with an external communication device.

DETAILED DESCRIPTION

Figure 1:
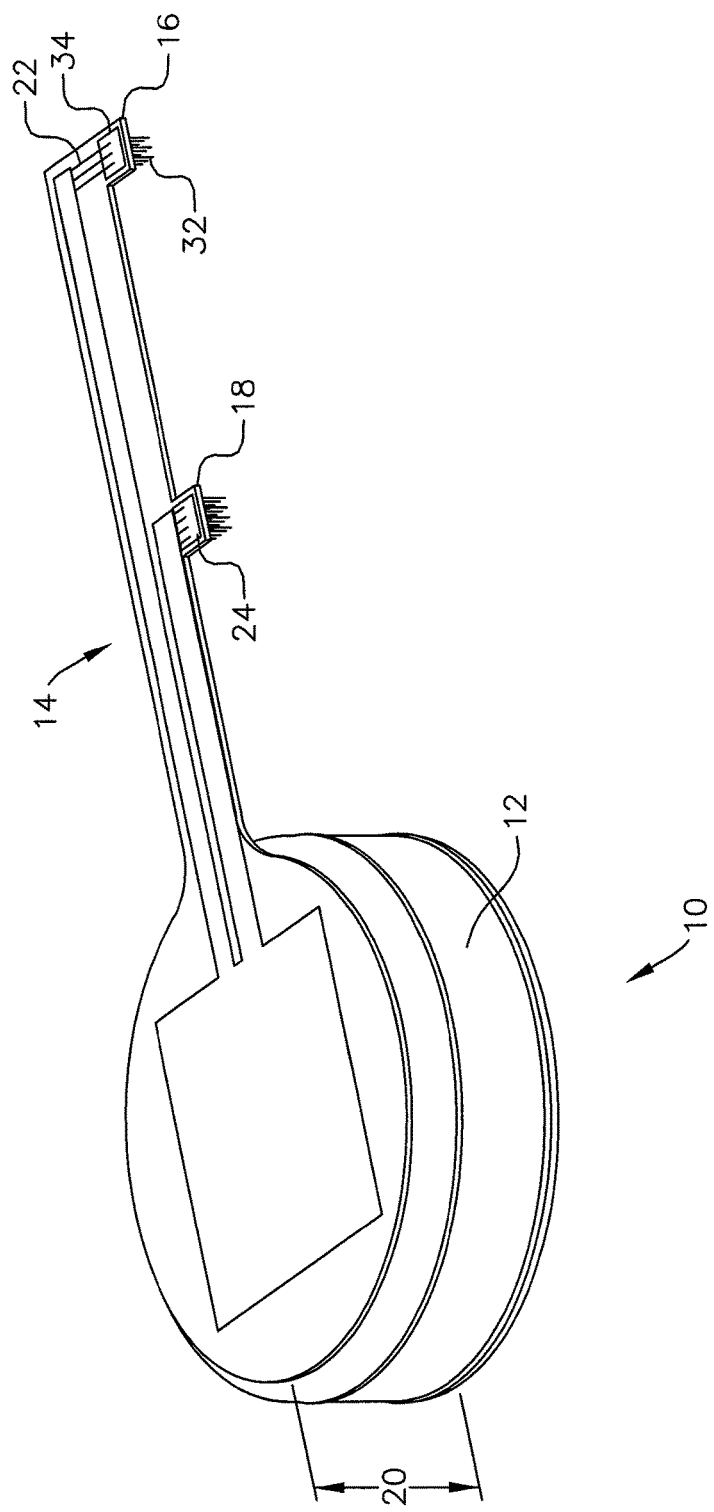
FIG. 1 is a front perspective view of an embodiment of a brain implant device in accordance with the present invention.

Turning first to FIG. 1 there is shown a representative perspective view of a brain implant device (BID) 10 implemented in accordance with an embodiment of the invention. Such device 10 comprises an electronics package assembly 12, an electrical conduit 14, and at least one electrode array 16. As viewed in FIG. 1, multiple electrode arrays are contemplated as exemplified by the addition of array 18. Still further, arrays coupled to conduit 14 are contemplated by the invention depending upon the nature and extent of the particular application.

As shown in FIG. 1 the assembly 12 is generally circular in shape, however, other shapes such as square or oval, as mere examples, are also contemplated by the invention. A circular shape for assembly 12 is preferable since, as will be shown later, the assembly 12 is typically embedded in a human skull which is typically most easily modified to accommodate a circular assembly by the use of a surgical drill. The diameter of the assembly 12 is in the range of about 15-25 mm and preferably about 20 mm. The axial thickness 20 is about 5 mm. The BID 10 is adapted to provide both sensory and stimulation capability to the motor cortex and the sensory cortex of the brain. As is recognized in the field, unique sites in the brain are dedicated for controlling and sensing reactions of corresponding body elements. For example, there are portions of the brain that are associated with toes, ankles, feet, wrists, fingers, eyelids, lips, and so on. To this end, the BID 10 includes 32 channels to control 32 individual body elements. Conceptually, the number of channels is far greater than 32 and is ultimately dictated by the electronic capacity of the assembly 12. Moreover, more than one BID may be utilized in one application thereby increasing overall BID capability accordingly.

Each channel comprises electronics for sensing body indicators such as neuron firing and muscle depolarization. Moreover, each channel comprises electronics to provide electrical sensing of the brain motor cortex and electrical stimulus to the brain's sensory cortex. The basic electronics sensory and stimulation functions are implemented, when considering radio frequency energy generation techniques, in accordance with the teachings of U.S. Pat. Nos. 5,358,514; 5,324,316; 5,193,539; and 5,193,540 which are assigned to the assignee hereof and which are incorporated herein by reference in their entireties. In addition, when considering battery powered energy generation techniques, the sensing and stimulation functions are implemented in accordance with U.S. Pat. No. 6,185,452 which is assigned to the assignee hereof and is incorporated herein by reference in its entirety.

Stimulus and sense signals directed to specific brain sites are provided by electrode array 16 [and other arrays when required]. Such signals are generated in assembly 12 and carried by conduit 14 to the specified brain sites. The conduit 14 preferably is a flexible multi-conductor conduit having dedicated conductors for each electrode (protuberance 32) in electrode array 16 [and 18 and so on, as required]. When configured in a bipolar mode, one conductor is used per electrode in an electrode pair with one electrode of the pair acting as the source and the other electrode of the pair acting as the return. In a unipolar mode, one conductor is used per electrode but the return is accomplished through body tissue and contact with a metallic surface on an assembly 12 [otherwise identified as an indifferent electrode].

As shown in FIG. 1 conductors 22 and 24 representing two of a plurality of conductors for array 16 and 18 respectively, extend from assembly 12 along conduit 14 to electrode array 16. Although several conductors shown for purposes of clarity, it is to be understood that a conductor exists for each electrode on an electrode array. The conduit 14 is preferably flexible, capable of following the contour of the brain between the location of assembly 12 and the selected site on the brain. The conduit 14 is capable of being shaped in a zigzag manner when such is required to meander between the assembly 12 and a desired brain site. A candidate conduit 14 is silicone rubber or polyimide with platinum conductors embedded in the silicone rubber, spaced apart so as to be insulated one from another. The conductors, although preferably formed of platinum, may be selected from materials such as, but not limited to, copper, gold, silver, and alloys thereof. The conductors are typically 1 mil in diameter and spaced apart one from an adjacent one about 1 mil.

Figure 2:
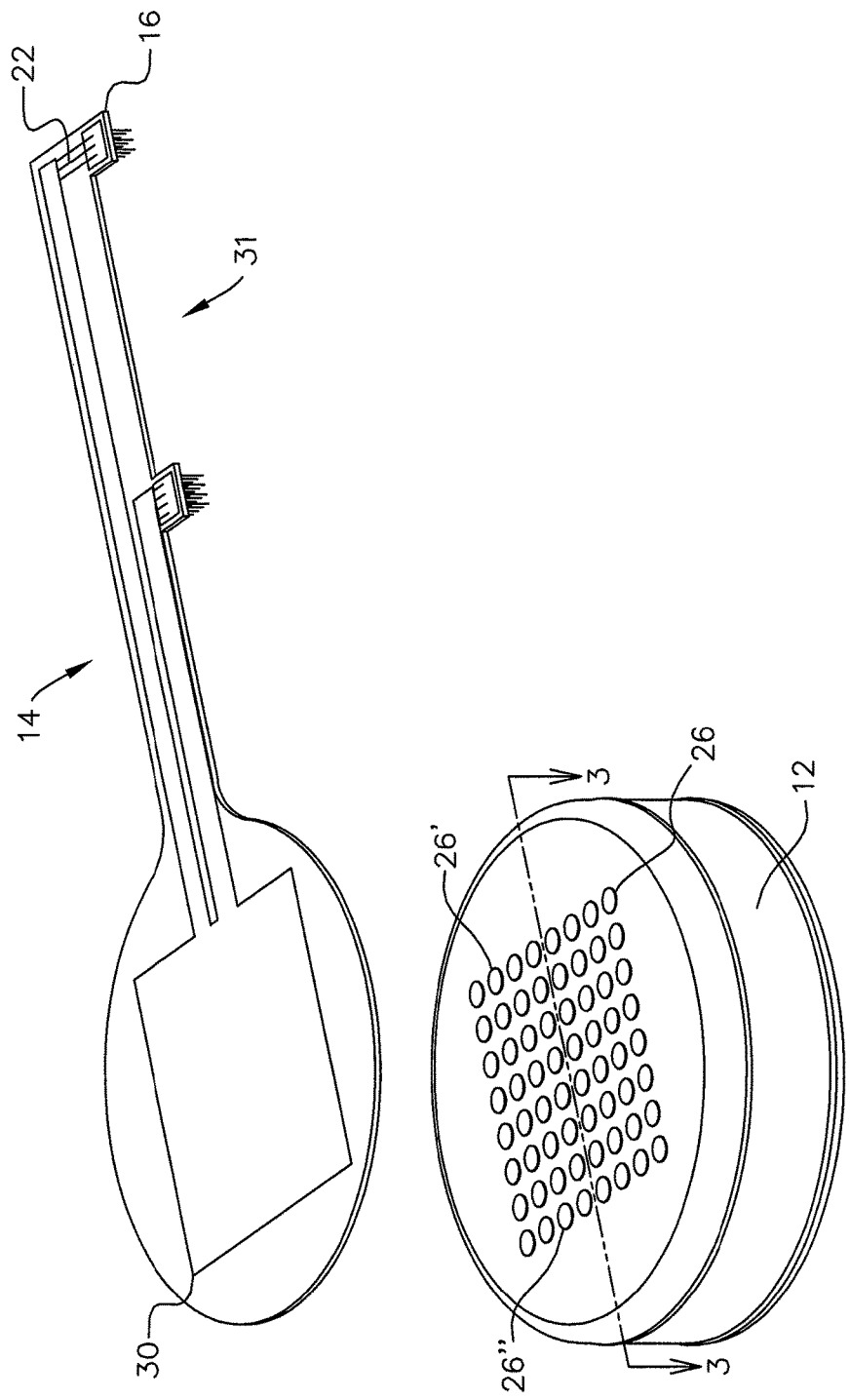
FIG. 2 is a front perspective exploded view of the invention of FIG. 1 with the conduit separated from assembly 12.

Transfer of electrical signals from assembly 12 to conduit 14 is by way of electrical connection between mating contacts on the assembly 12 and conduit 14. As shown in FIG. 2 contacts 26, 26', 26" and so on, for each contact are disposed on an outer surface 28 of assembly 12. Corresponding and mating contacts on conduit 14 are positioned at the conduit proximal end 30 so as to be in registration with corresponding contacts on assembly 12. Accordingly, signals appearing on contacts 26, 26', 26" and so on for all contacts, are transferred to corresponding contacts on conduit distal end 31. Conduit 14 may be adhered to assembly 12 by methods known in the art, such as for example, by medical adhesives or bonding suitable for medical applications involving implantable devices. An alternate technique for adhering the conduit 14 to the assembly 12 is by means of hermetically sealed electrical feedthroughs such as described in U.S. Pat. Nos. 5,750,926 and 5,640,764 both assigned to the assignee hereof and incorporated herein in their entireties by reference.

Still further techniques for interconnecting sensory and stimulation electrodes to an electronics assembly by means of a thin flexible circuit ribbon are described in detail in U.S. Pat. No. 7,142,909 incorporated herein by reference in its entirety.

The electrode array 16 [18 and others as needed] includes a plurality of electrically conductive protuberances 32 extending substantially perpendicularly from array base 34. The individual conductors 22 are electrically connected to corresponding and respective ones of the protuberances 32. The distal tip of protuberance 32 is sufficiently small and sharp to be capable of making electrical contact with a single cellular component of tissue, and in particular with brain tissue. The protuberances 32 extend from array base 34 with a range of heights from approximately 0.5 micrometers to about 100 micrometers. The protuberances 32 are adjacently spaced on array base 34 from approximately 0.5 micrometers to about 1000 micrometers from each other. Each protuberance 32 has a biocompatible insulating coat exclusive of the protuberance tip. An electrode array as presented herein is described in detail in U.S. Pat. No. 4,969,468 which is assigned to the assignee hereof and is incorporated herein by reference in its entirety.

Figure 3:
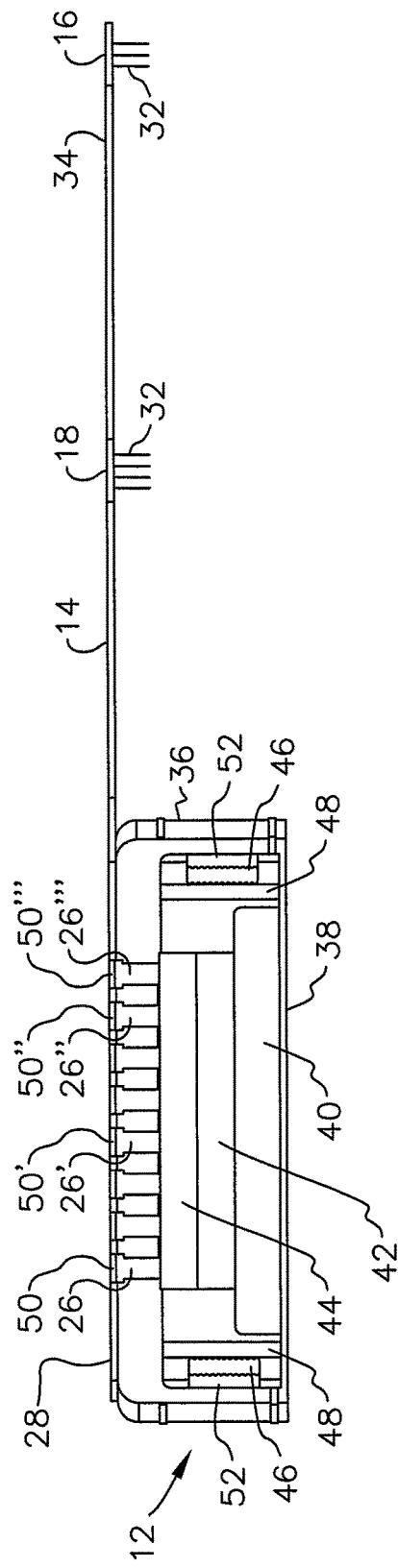
FIG. 3 is a front cross-sectional view taken along lines 3-3 of FIG. 2.

Signals monitored and supplied to electrode array 16 are processed by assembly 12 which is a hermetically sealed container comprising a ceramic cup 36 closed at the open end by metallic cover plate 38. FIG. 3 is a cross-sectional view of the assembly 12 of FIG. 2 taken along line 3-3. The ceramic cup 36 is comprised of an insulating ceramic, such as for example, zirconia, and metallic plate 38 is secured to cup 36 by means of brazing in a manner to hermetically seal the contents of the cup 36 from an external environment.

Other ceramic materials may include stabilized zirconia, partially stabilized zirconia, yttria-stabilized zirconia, magnesium, calcium stabilized zirconia alumina, silicon nitride, silicon carbide, titanium carbide, tungsten carbide, titanium nitride, silicon oxynitride graphite, titanium diboride, boron nitride and molybdenum disilicide. Prior to brazing, a "getter" may be introduced into the cup, so as to maintain the interior region of the cup free of any gases or liquid contaminant that may be introduced during manufacture and assembly. The metallic plate 38 may comprise Ti64 titanium and a titanium containing alloy.

The brazing process is any one of a number of processes known in the art such as that described in U.S. Pat. No. 6,221,513. Contained within assembly 12 is battery 40, timing and frequency source crystal 42, and chip stack 44. Battery 40 may be a rechargeable battery having a power capacity in the range of about 2 milliamp hours per cubic centimeter. Candidate batteries may be formed of LI-I or LI-I-SN. The battery is sized to be capable of providing power to a plurality of microsensor and mircostimulator electronics [hereinafter "micro device electronics"] as well as to system electronics including processor and telemetry circuits. Advantageously the battery 40 serves as a common power supply for each of the micro device electronics. In this manner, a single recharging circuit may be used in place of individual recharging circuits for each micro device electronics. The recharging circuit comprises coil 46 which is wrapped around ferrite ring 48 and is interconnected to a corresponding control chip in chip stack 44. Control of battery charging by means of the battery control chip is implemented in a manner similar to that as taught in U.S. Pat. No. 6,185,452. The coil 46 is capable of being magnetically coupled to an external device that transmits a magnetic, ultrasonic or RF command signal for at least charging battery 40. Accordingly, the same coil 46 may be used for charging the rechargeable battery 40 and for providing control and command signals in a manner consistent with the teachings of U.S. Pat. No. 6,185,452.

Referring again to FIG. 3 there is shown a capacitor and crystal assembly 42 mounted in proximity to battery 40. In particular, the crystal assembly houses a crystal oscillator, serving as a very accurate clock source, as to provide real time scheduling and to provide a receiver and transmitter with a constant and accurate frequency source. Additionally, each of the 32 channels or the number of channels selected for a particular application is coupled to this crystal oscillator as to provide complete frequency synchronization throughout and between all selected channels. Accordingly, any potential frequency mismatch between channels may be avoided by having a common frequency source or clock for all selected channels. Use of a crystal, in a task scheduling mode for example, is described in U.S. Pat. No. 6,164,284.

The capacitors mounted on assembly 42 are arranged and controlled to provide stimulation pulses at the appropriate site on the brain sensory cortex. Each selected channel includes a corresponding capacitor sized and charged to a stored energy value to provide brain detectable signals to corresponding locations on the sensor cortex. Each of the capacitors in assembly 42 are electrically coupled to respective ones of the contact 26, 26', and 26", etc. through gating circuitry contained in chip stack assembly 44. Accordingly, the particular capacitor that is connected through or by means of the chip set is dependant upon which of the protuberances 32 is designated to receive a stimulation signal provided by the corresponding charged capacitor.

Mounted in proximity to the capacitors and crystal assembly 42 is chip stack assembly 44. The preferable packaging technique for chip stack assembly 44 is vertical stacking for the integrated circuits/chips and for interconnection of conductors to interconnect selected contacts of different ones of the chips in the chip stack. A technique for such chip stacking and interconnect is described in U.S. Pat. No. 7,071,546 assigned to the assignee hereof and incorporated herein in its entirety by reference. The chip stack 44 contains communications and control electronics including amplifier electronics to enable sensing signals from and stimulation of, a selected number of brain sites, depending upon the muscle group selected to be activated. The present embodiment is configured to contain 32 individual amplifiers, however, 64 and 128 amplifiers and beyond are well within the contemplation of the invention. The circuit design requirements and configuration to undertake the stimulation and sensing functions are described in U.S. Pat. Nos. 5,358,514; 5,324,316; 5,193,539; and 5,193,540 as referenced above.

Figure 4:
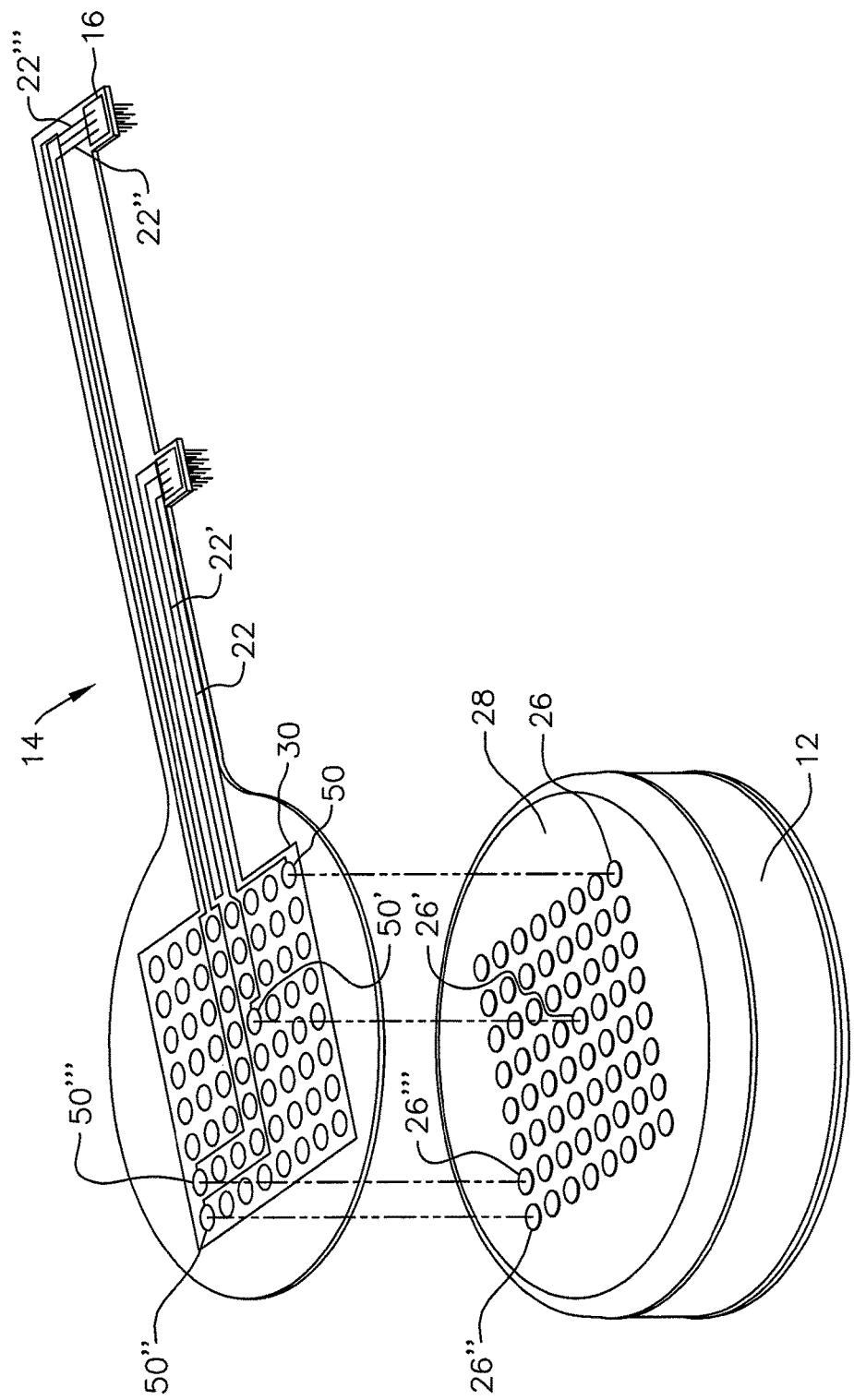
FIG. 4 is a front perspective exploded view of the invention of FIG. 1 with the conduit separated from assembly 12 and showing selected wire interconnects.

Sensing and stimulation signals processed by chip stack 44 are carried from the selected brain sites to assembly 12 by means of conduit 14. As previously described, although not restricted to a specific material, conduit 14 is preferably formed of a flexible thin film electrically insulating material such as for example, Kapton or silicone. Kapton is a registered trademark of E.I. DuPont Nemours Company. Embedded within the Kapton are thin flexible electrically conductive wires such as platinum or gold or copper or alloys thereof that extend the length of the conduit 14 from the connection point with the protuberances 32 on electrode array 16 [and 18, etc. if present] to the corresponding contact 26 [26', 26", etc.] on assembly 12. As previously described, the conduit 14 is sufficiently flexible to conform to the contour of the tissue below the surface of the skull and maybe even configured in a serpentine like fashion to allow for a slight contraction or extension of the conduit without the fear of dislodgement of the protuberances 32 from the contact points on the brain. Each of the conductive wires embedded within the Kapton, terminates at different specific ones of contacts located at the proximal end 30. For example, and with reference to FIG. 4, conductor wire 22 is electrically and conductively attached to contact 50 on the proximal end of conduit 14. Similarly, conductor wires 22', 22", and 22''' are electrically conductively attached to contacts 50', 50", and 50''' respectively. When the conduit 14 is mounted together in contact with the assembly 12, conduit 14 is oriented relative to the assembly 12 such that the contacts 50, 50', 50" and 50''', etc., are in registration and alignment with corresponding contacts 26, 26', 26", and 26''', etc., on assembly outer surface 28. Reliable conductivity between contacts 50, 50', etc. and 26, 26', etc. respectively, may be accomplished, for example, through the use of "soft bumps" each bump being positioned between each respective contact 50 and 26. The soft bumps are formed of soft malleable electrically conductive material so that when the conduit proximal end 30 and the assembly 12 are urged together, the bumps are slightly deformed due to contact pressure and reliable electrical connections are established between conduit contacts and the assembly contacts. This and other techniques known in the art may be used to establish reliable electrical contacts between the conduit 14 and assembly 12.

The conduit 14 may carry upwards of 128 wires and beyond, depending upon individual system design requirements. In such case, each amplifier in chip set 44 may be selectively attached to five different contacts, that is, two contacts for a sensing function, two contacts for a stimulation function, and one contact to an indifferent electrode. Switching between each of these functional capabilities may be through switching techniques used and known in the art. Communication with external electronics is by way of antenna 52. Antenna 52 extends circumferentially about coil 46, typically, in a dipole antenna configuration. The antenna is electrically coupled to receiver and transmitter electronics [not shown] in chip set 44, for communicating command and control signals to assembly 12 and to transmit sensory and status signals from assembly 12 to an external control circuit [not shown]. Communication frequencies, although not being limited to, are preferably between 100 to 900 MHz. Communication techniques and signal processing techniques are consistent with those described in the above referenced patents assigned to the assignee hereof.

Although only a dipole antenna configuration has been described it is to be understood that other antenna configurations are contemplated by the invention as well. For example, one of the conductors 22 may be used as a single wire antenna in place of the dipole antenna 52. In such case, the conductor 22 preferably, would not be coupled to a respective protuberance 32. In an alternate embodiment, for example, the outer surface 28 may be formed of a metallic material and the contacts 26, 26', etc. may be surrounded by electrically insulating feedthroughs known in the art. In such case, the contacts 26 and 50 and so on, are electrically insulated from the surface 28 and metallic cover plate 38 may be coupled to a RF generator contained on chip set 44, so as to form an antenna to transmit signals generated by such RF generator. To communicate with external electronics, the RF generator as well as, surface 28 and metallic cover plate 38, may be coupled to chip set 44 in a manner previously described, with the surface 28 and cover plate 38 providing radiating antenna surfaces.

In practice, the BID 10 is used in conjunction with a master controller and at least one implanted microstimulator/microsensor. A master controller is capable of receiving signals from the BID 10 interpreting whether it is a motor cortex signal, and if so, transmitting a stimulation command to a corresponding selected microstimulator to stimulate a target muscle or target nerve. In the event that the received signal is a sensory signal, the master controller is capable of transmitting a "recognition" signal generated by the target muscle or target nerve to the BID 10 which then provides a signal to the sensory cortex to indicate to the brain that commanded activity has occurred. Functional capability and electronic implementation for the master controller, or as alternately identified as the system control unit, may be found in U.S. Pat. Nos. 6,208,894 and 6,315,721 assigned to the assignee hereof and incorporated herein in their entireties by reference.

Figure 5:
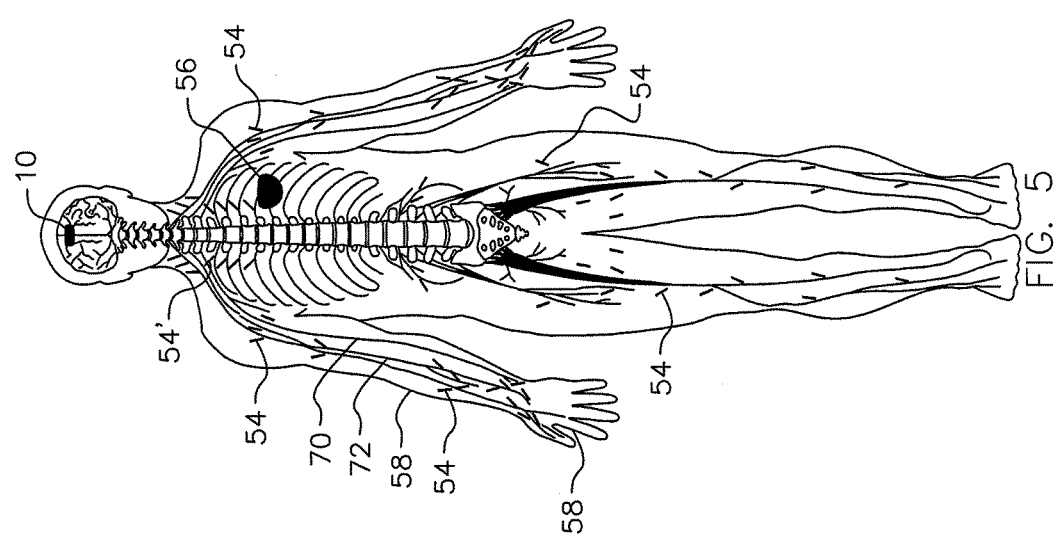
FIG. 5 is a representation of a human body showing the placement of implanted micro devices.

Continuity of motor cortex commands from the brain to a selected muscle/nerve group in a living body may be interrupted if the nerve pathway is severed. In such case, desired commanded muscular reaction is inhibited. FIG. 5 shows the placement of a plurality of microstimulators/microsensors 54 throughout a human body each placed in proximity to a muscle/nerve to be stimulated and locations where corresponding responsive reactions are to be sensed. Although only several microstimulators/microsensors are numerically identified, it is to be understood that all devices shown are equivalent in function. Further, master controller 56 is shown as being implanted, however, it is to be understood that the master controller 56 may also be located outside the body within sufficient proximity to the body such that reliable wireless communication with the microstimulator/microsensor 54 and BID 10 may be undertaken.

Figure 6:
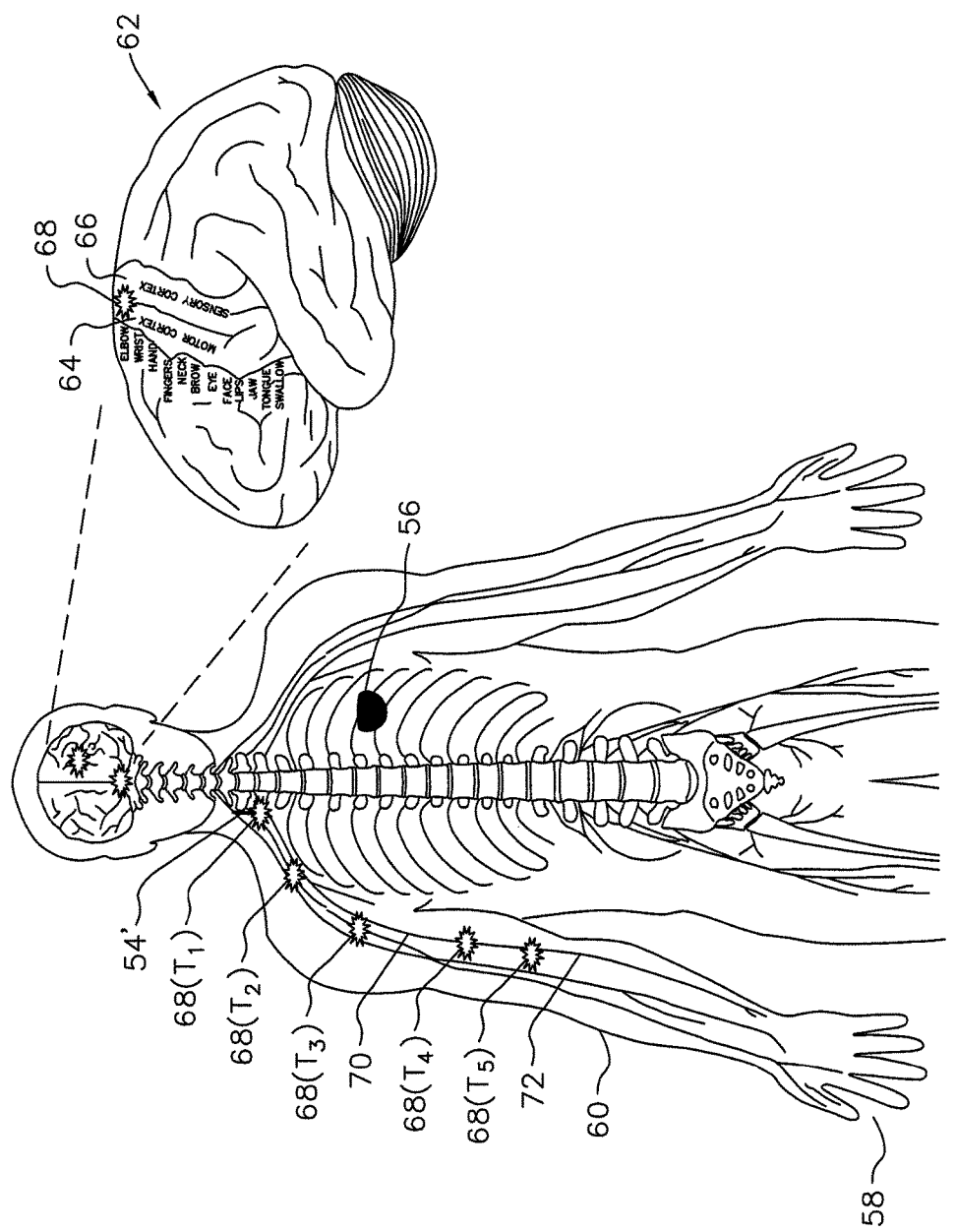
FIG. 6 is a representation of a human body showing the progression of signals along a selected nerve path.

To explain the overall process of directed stimulation and the resulting sensory signal feedback, an example would prove helpful. With reference to FIG. 6 and for purposes of illustration, assume that the lifting of a hand 58 by means of rotation of elbow 60 is commanded. It is understood that the brain 62 as shown in FIG. 6 contains a motor cortex 64 and a sensory cortex 66.

Broadly described, defined brain sites are dedicated to specific body locations and elements. As shown in FIG. 6, identified portions of the motor cortex are dedicated to, for example, the elbow, wrist, hand, fingers, etc. with each site further divided [not shown] to right and left elbows, right and left wrists, etc. and the specific fingers on each hand, etc. The sensory cortex 66 has corresponding sites to each motor cortex site. When the brain commands selected activity, such as rotation of an elbow, corresponding neuron activity occurs in the corresponding motor cortex site. Such neuron activity normally translates into stimulation of nerves dedicated to muscle groups controlling rotary motion of the elbow, and under normal conditions, the elbow 60 rotates so that hand 58 lifts from its prior position to the desired position. The progression of neural signals 68, originating in the brain 62 and moving down the relevant nerve path 70, to the corresponding elbow muscle/nerve group 72, is shown in FIG. 6 as 68 [$T_1$], 68 [$T_2$], 68 [$T_3$], etc., where $T_1 < T_2 < T_3$, etc. Muscle movement and the resulting muscular depolarization causes response signal carried by the elbow muscle group nerve to be transmitted back to the elbow site on the sensory cortex to provide a feedback signal to the brain indicating that the commanded action has occurred.

Figure 7:
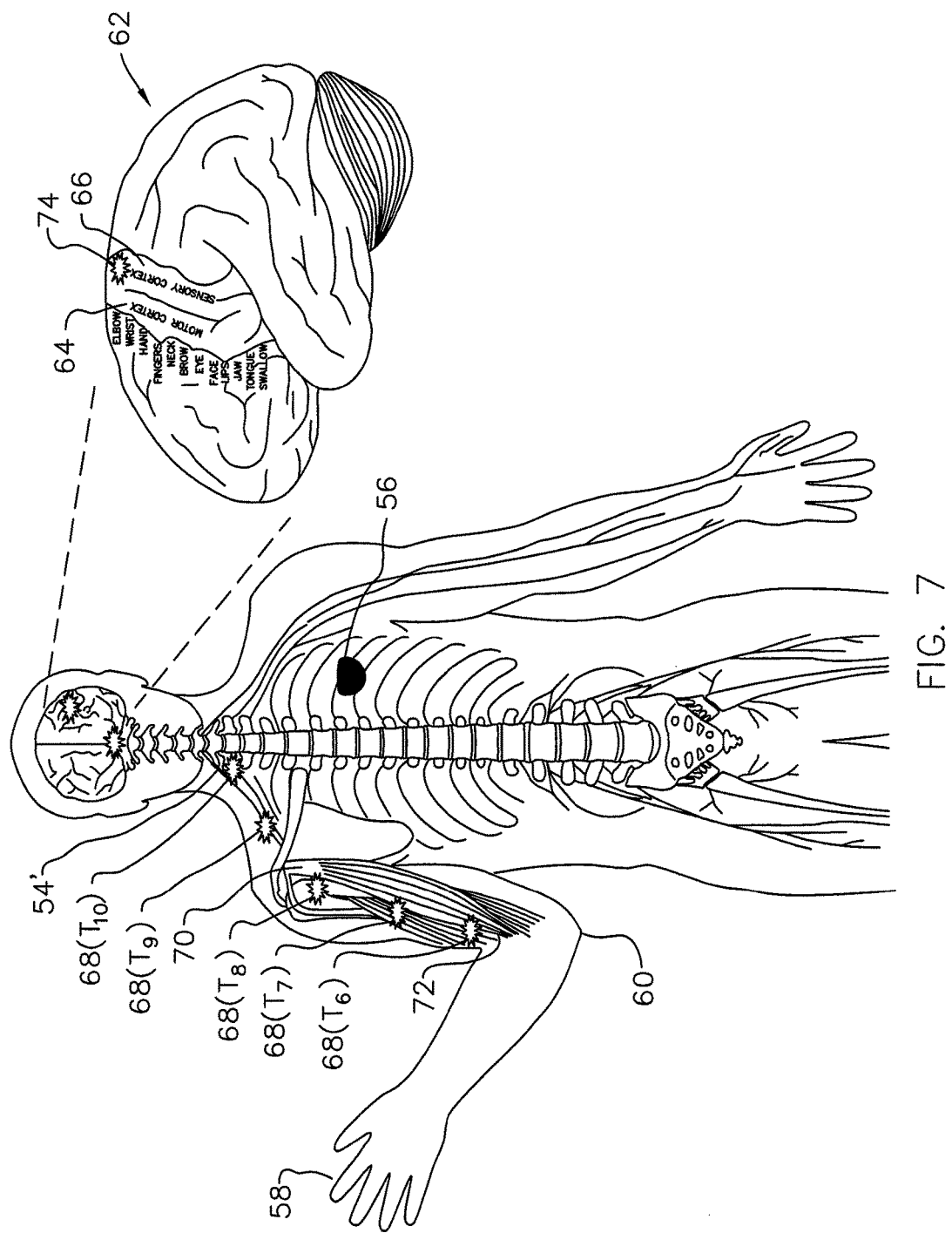
FIG. 7 is a further representation of a human body showing the progression of signals along a nerve path and their relationship to the brain's motor and sensory cortex.

FIG. 7 shows hand 58 raised in position due to the rotation of elbow 60. The progression of the depolarization signal 74 back to the corresponding elbow site in the brain's sensory cortex 66 is shown by 74 [$T_6$], 74 [$T_7$], 74 [$T_8$], etc. where $T_6 < T_7 < T_8$ etc. In the event that the relevant nerve path is severed, it is understood that the control signal will not reach the selected muscle group, and the commanded action will not occur. In such case, a microstimulator/microsensor 54' [see FIGS. 5, 6 and 7] is placed downstream from where nerve 70 is severed. The microstimulator/microsensor 54' serves to apply, when commanded to do so, an electrical stimulation signal on nerve 70 similar to that normally occurring after the issuance of a command from the brain. To that end, a protuberance 32 on array 16 is positioned precisely (see FIG. 9) on the motor cortex 64 to detect "elbow" signals and to carry such signals corresponding to brain neuron activity to BID 10. BID 10 transmits, typically by way of a wireless communication channel, a uniquely coded message corresponding to signals detected at the "elbow" site of the brain motor cortex 64, to master controller 56. The master controller 56 identifies the coded message and dispatches a command signal to the specific microstimulator/microsensor, and in this example 54', positioned to stimulate the nerve (in this example) 70 that causes the initiation of the rotation of elbow 60. Upon completion of rotation of elbow 60, a depolarization signal is emitted by the muscle group 72 which then travels up nerve 70 to microstimulator/microsensor 54'. Because the nerve 70 is severed at this location, the signal does not proceed to the sensory cortex. The depolarization signal, however, is detected by microstimulator/microsensor 54' which then dispatches a corresponding signal reception acknowledgement to master controller 56. The master controller 56 then dispatches a coded message, as in the downlink mode by way of wireless communication, to BID 10. The BID 10 then provides a signal via conduit 14 to the protuberances 32 that is positioned to contact the brain site devoted to the elbow on the brain's sensory cortex 66. In this manner, and effective feedback signal is applied to the brain, indicating that the commanded body activity has indeed been accomplished.

In an alternate embodiment of the present invention, the BID 10 is configured to transmit command signals and receive response signals directly from a microstimulator/microsensor. In that regard, signals at a particular brain motor cortex site indicating desired activity for the corresponding body element, are carried to the BID 10 by way of conduit 14. Signals processed by the BID 10 are dispatched, typically by wireless communication to the specific microstimulator/microsensor 54 dedicated to stimulate and monitor the body element corresponding to the particular sensory cortex activity. Upon receipt of the command signal, microstimulator/microsensor 54' [for the present example] provides a stimulation signal to the nerve/muscle group dedicated to undertake the commanded activity. Once the activity has been completed, the depolarization signal is sensed by microstimulator/microsensor 54', and an acknowledgement is dispatched again by wireless communication back to the BID 10 which then provides an acknowledgement signal to the brain's sensory cortex dedicated to the body element activated.

Figure 8:
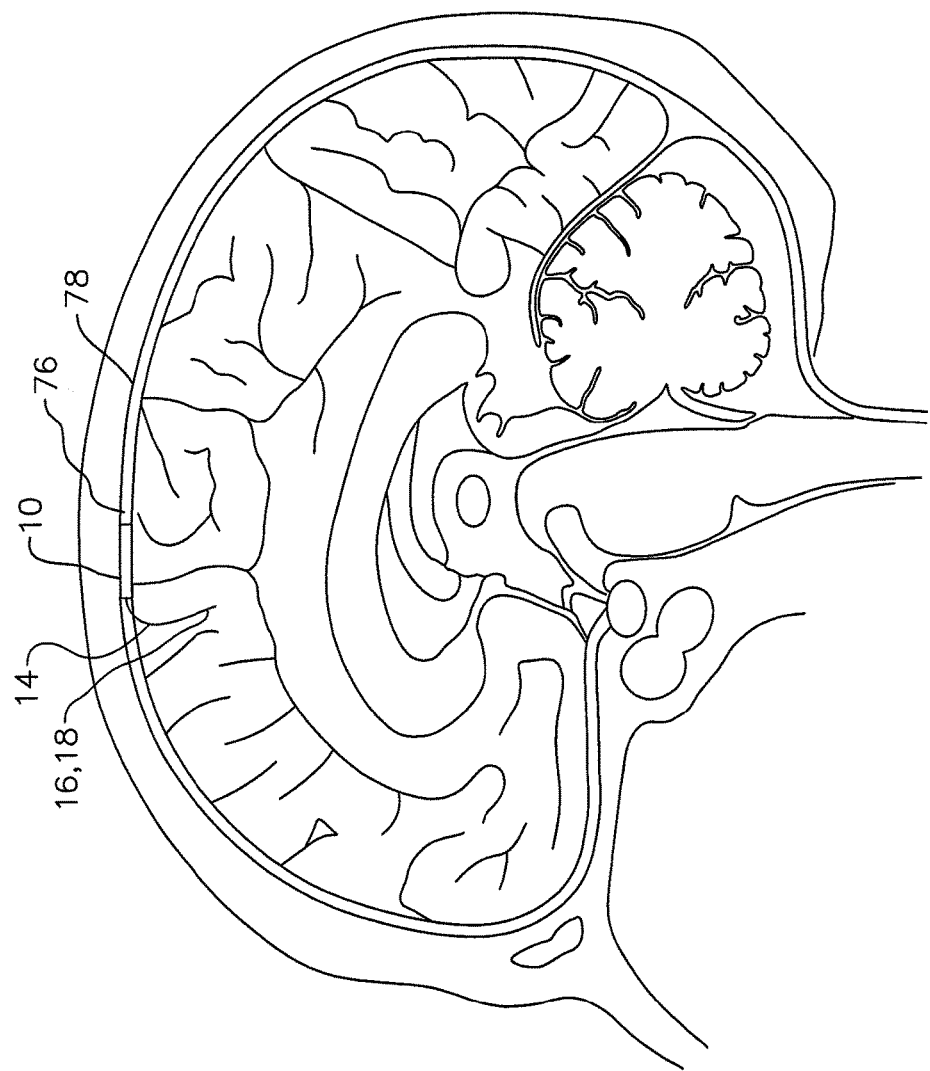
FIG. 8 is a cross-section of a human skull showing the location of a brain implant device.

In a typical application, the BID 10 is embedded below the external surface of the skull. In that regard, reference is made to FIG. 8 showing BID 10 located below the interior surface 76 of skull 78. Command and control signals, as previously described, are conveyed between brain sites monitored by electrode arrays 16 and 18 on conduit 14. The materials comprising the BID 10, conduit 14 and electrode array 16 and 18 are biocompatible and sealed to minimize the risk of infection to the patient. Surgical techniques used in implanting the BID and associated accessories are known in the art. In yet another embodiment, the BID may be located external of the skull with the conduit 14 being placed in position below the skull and in contact with the motor cortex and the sensory cortex.

Figure 9:
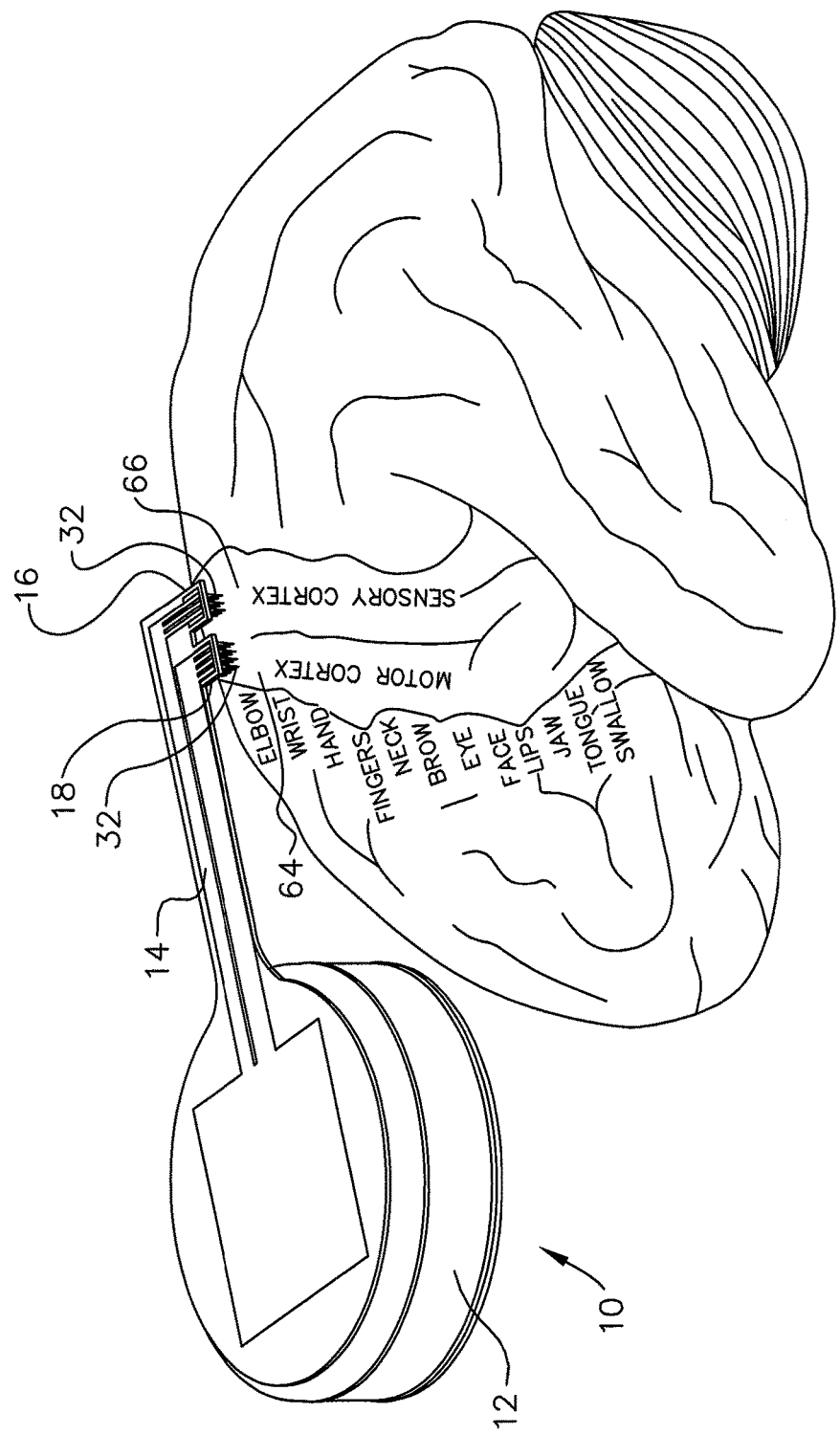
FIG. 9 is a perspective view of a brain implant device and the position of electrode arrays on the brain's motor and sensory cortex.

FIG. 9 is an illustration of the placement of two electrode arrays 16 and 18 used in conjunction with the BID 10 whereby electrode array 16 is disposed over the brain's motor cortex 64 and electrode 18 is disposed over the brain's sensory cortex 66. It is to be understood that using two electrode arrays is a design choice dependant upon the number of body elements to be controlled and the distance between the corresponding motor cortex and sensory cortex sites. For certain applications, where for example, only one body element is to be controlled, attachment to both motor cortex and sensory cortex sites may be satisfied using only a single electrode array.

To accommodate sensing rapidly occurring neurological signals sampling of such neurological signals may be undertaken at rates in the range of about 30,000-50,000 samples per second. This range may be expanded depending upon the nature of the neurological signal sensed. For example, signals occurring during periods of very slow activity, such as sleeping, may call for a much slower sampling rate, whereas periods of very fast activity may call for faster sampling rates. Considering a sampling rate of 40,000 samples per second or 400 samples per 10 milliseconds and using an 8-bit word per sample, then without any data reduction scheme the electronics contained within chip stack 44 would be required to process 3,200 bits of information per millisecond. Although doable, the electronics size requirements imposed by this data handling capability conflict with the miniaturization objective for chip stack 44 and ultimately for the assembly 12. Accordingly, a "window circuit" consistent with the teachings put forth in U.S. Pat. No. 6,990,372 and incorporated herein in its entirety and is utilized in the electronics of chip stack 44. The window circuit configured to include low and high magnitude signal threshold levels coupled with a rectifying and averaging process reduces a large number of neuron firing (neurological signals) for 10 milliseconds to a much lower but representative number. The window circuit essentially may be described as event detection circuitry where the events are the detected magnitudes of the several neurological signals that exceed the preselected threshold settings and further includes an event counter that counts the number of detected events over a preselected time interval. These detected events may be further analyzed by determining the average number events per time interval as a measure of the detected neurological signals. For example, the 3,200 bits of information per 1 millisecond sample interval previously discussed may be reduced to about 8 bits. Low and high thresholds described in U.S. Pat. No. 6,990,372 may be adjusted to achieve the above described reduction of bit information processed. Further separation of the high and low threshold values can reduce the number of bits in the range of 2 to 3 bits. An additional advantage of the data reduction resulting from the use of the window circuit is that autocorrelation signal processing is not necessary and therefore not incorporated in the electronic processing scheme which further reduces the amount of processing and therefore decreasing the overall size of the electronics necessary for chip stack 44. In effect, the window circuit implementation reduces the vast amount of data to an "essence signal" by taking advantage of nerve spike signals and developing an average of such spike signals.

Figure 10:
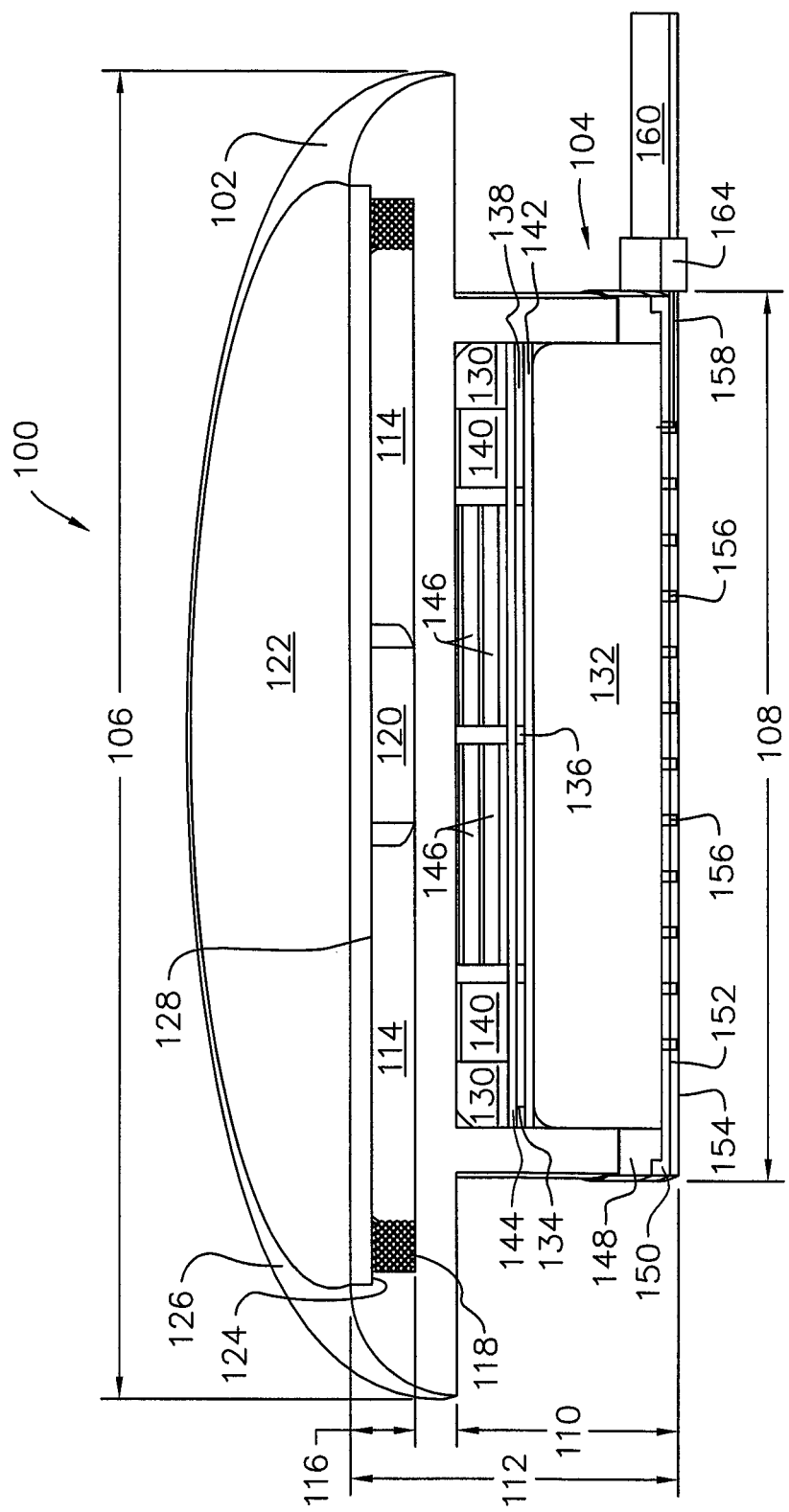
FIG. 10 is a front cross-sectional perspective view of an alternate embodiment of the present invention.

With reference now to FIG. 10 there is shown an alternate embodiment of the present invention. The brain implant device 100 is somewhat "mushroom" shaped having a cap portion 102 and a stem portion 104. Although not restricted to any specific material, a suitable material for the cap and stem portion of device 100, is zirconia. Although not restricted to unique dimensions and shapes the cap portion 102 preferably is circular in shape having a diameter 106 of about 30 mm. The stem portion 104 preferably is circular having a diameter 108 of about 20 mm. The stem portion 104 has an overall height dimension 110 (including disk 152 and insulator 154) being about 5 mm and the device 100 has an overall height dimension 112 being about 7.5 mm. The cap portion 102 includes a disk shaped recess 114 extending into the cap a dimension 116 being about 1.25 mm.

Disposed along the periphery of recess 114 is coil 118 as will be described below. Coil 118 is adapted for magnetic coupling with an external time varying magnetic field for recharging energy storage means contained in a device 100. Located Within the recess 114 is permanent magnet 120. Magnet 120 is positioned within the recess 114 so as to optimize alignment of the magnetic field with respect to the coil 118 to maximize magnetic coupling between the magnetic field and the coil. The magnet 120 may be secured in place by any one of a number of techniques know in the art including, for example, an adhesive capable of adhering metal to a ceramic material.

To seal the recess 114 from an outside environment, a cover piece 122 is positioned to rest against circular lip 124 that extends slightly inward in the recess to form a shelf to support cover piece 122.

The thickness of the cover piece 122 and the depth of the circular lip 124 that extends (measured downward) from the outer contour surface 126 of cap portion 102 is sized such that with the corner piece in place a relatively continuous outer surface 126 is maintained. The cover piece 122 may be secured in place by use of a number of techniques such as, for example, a bonding material capable of bonding ceramics together at low temperature. A candidate material for active solder joining of ceramics is S-Bond TM 200 available from Material Resource International of Lansdale, Pa., USA.

Located on the inside face of cover piece 122 is an antenna 128 (now shown in FIG. 10, see FIGS. 15-18) in accordance with the principals described for antenna 52. Although antenna 52 is described as extending circumferentially about coil 46 it is to be understood that antenna 128 may be disposed in a number of geometries (FIGS. 15-18, as mere examples) to accomplish the transmission reception capability of the antenna 128.

The stem portion 104 defines an interior cavity 130 sized to house device electronics. More particularly, cavity 130 includes battery 132 comprising a structure and design similar to that of battery 40. Mounted above battery 132 are transmitter/receiver chip 134, crystal 136 and battery management chip 138. The battery management chip 138 provides supervisory control over the battery charge state and prevents overcharging of the battery during the charging process. Moreover, chip 138 provides voltage regulation to the battery output to maintain device electronics with a substantially constant voltage source. Voltage charging control and voltage regulation is accomplished by chip 138 in a manner consistent with that described for the embodiment of FIG. 1.

Crystal 136 provides a constant frequency signal source of use in data processing, timing, clocking, gating, and telemetry transmission and receiving functions. The transmitter/receiver chip 134, crystal 136, and battery management chip 138 are mounted on board 142. Immediately adjacent to board 142 is board 144 upon which is mounted capacitors 140 and preamplifier and amplifier chips 146. The function of transmitter/receiver chip 134, capacitors 140, and preamplifier and amplifier chips 146 is consistent with that described for the embodiment of FIG. 1 and thus will not be repeated here and again.

A circumferential ring 148 is position at the base 150 of stem portion 104. Preferably the ring 148 is formed of a titanium material such as Ti64 capable of being brazed to a ceramic material. Ring 148 is brazed to stem portion 104 using brazing techniques well known in the art. A circular disk 152 preferably formed of Ti64 is sized to fit against ring 148 and provide a complete seal between the internal region of stem portion 104 and the external environment.

The disk 152 is secured to ring 148 by means of a laser weld in a manner to insulate the internal region of the stem portion 104 from entry of any external fluids and the like. Attached to disk 152 is a common material insulator 154 preferably made of Kapton that extends over the entire outward facing surface of disk 152. Attachment of insulator 154 to disk 152 may be accomplished by any one of a number of techniques known in the art.

Figure 11:
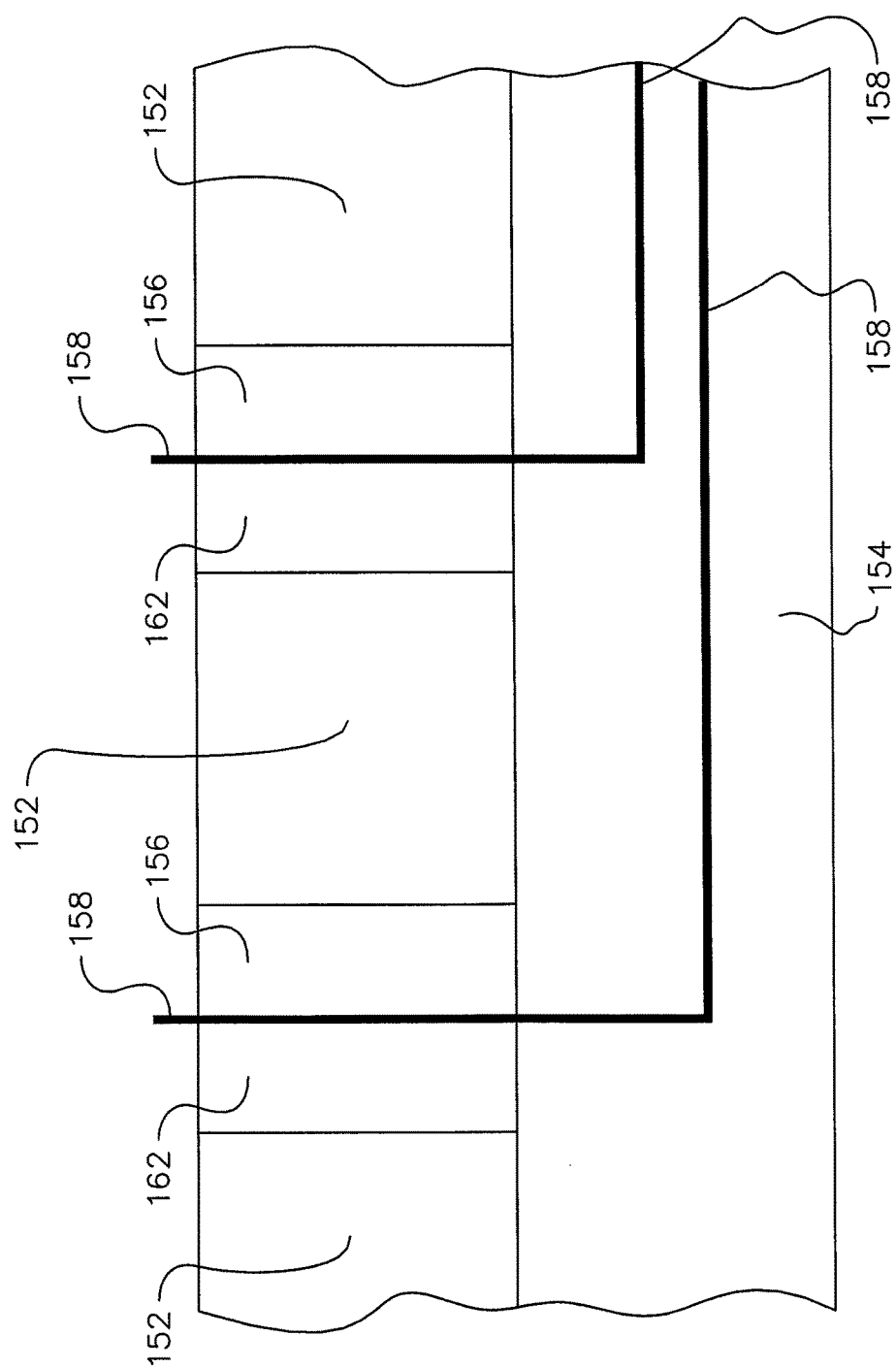
FIG. 11 is an expanded view of the conductor containing passageways of the invention of FIG. 10.

As shown in the partial schematic view of FIG. 11, distributed across the disk 152 and insulator 154 are a plurality of passage ways 156 (of which only two are identified in FIGS. 10 and 11) through which individual conductors 158 pass from the interior of device 100 to conduit 160. An insulating material such as glass 162 is contained within the passage way and surrounds the conductors 158 to maintain the individual conductors in place and electrically insulated from the circular disk 152. The individual conductors 158 pass through the insulator 154 and terminate at connector 164. Connector 164 may be one of a number of separable devices permitting conduit 160 to be detached and reattached to the connector 164. Conduit 160 is similar in structure and characteristics as conduit 14 and thus a description of conduit 160 need not be repeated herein again. The conductors 158, although not shown as being coupled to preamplifier and amplifier chips 146, it is to be understood that the conductors are routed to respective amplifiers to provide the sensing and stimulation function provided by device 100.

Figure 12:
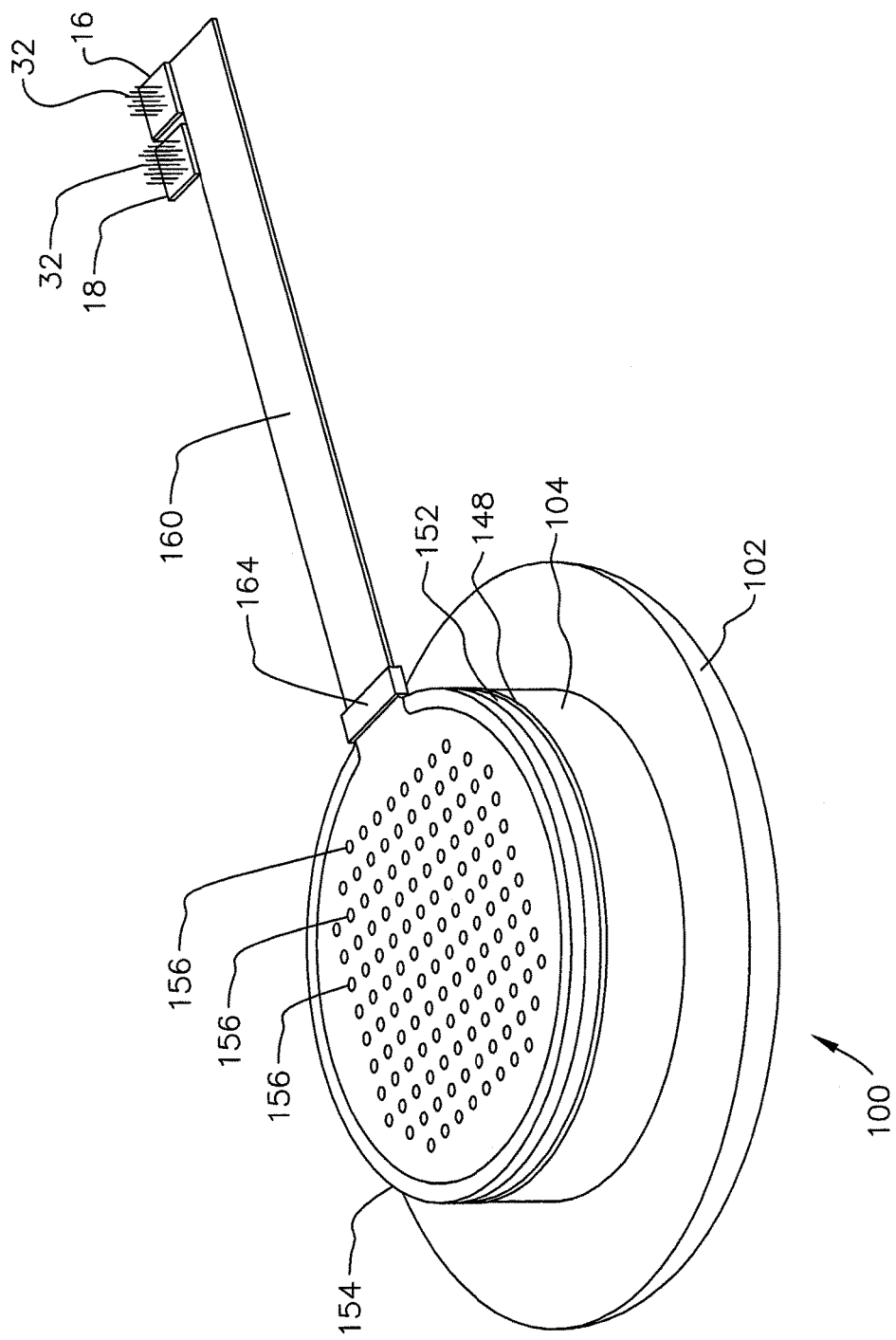
FIG. 12 is a front perspective view of the underside of the invention of FIG. 10.

Referring to FIG. 12 there is shown assembled in perspective view the underside of device 100. As shown with the insulator 154 partially cut away, passage ways 156 are disposed throughout circular disk 152, the conductors 158 are positioned within the insulator 154 so as to be electrically isolated one from the other as they traverse the insulator 154 and conduit 160. Although not shown, it is to be understood the conductors 158 are positioned within the device 100 from the insulator 154 to respective preamplifiers and amplifiers 146.

Figure 13:
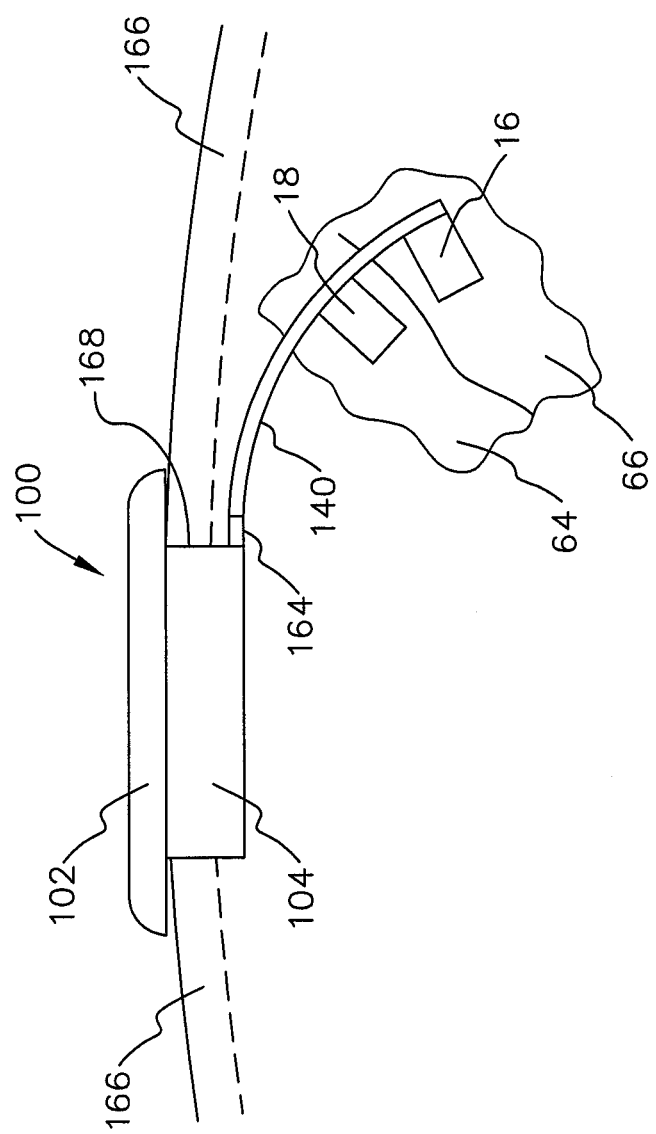
FIG. 13 is a partial cutaway view of a human skull including an implanted brain implant device.

With reference to FIG. 13 the device 100 is shown positioned in place in skull 166. For purpose of clarity, only the skull bone 166 of a mammalian head is shown. In one approach a hole 168 slightly greater in diameter than the diameter of stem 104 is drilled in the skull. Subsequentially conduit 160 is placed in the interior of the skull such that electrode arrays 16 (and 18 if included) is positioned in contact with the motor cortex 64 and/or sensory cortex 66 as desired. The device 100 may be secured in place by a compression fit whereby the hole 168 in the skull is marginally smaller in diameter than the diameter of the stem portion 104 and the gripping action of the skull against the stem portion 104 maintains the device 100 in place. Another one of a number of approaches known in the art to secure device 100 to the skull is by the use of a medical adhesive applied to the stem portion 104 with sufficient adhesive strength to keep the device 100 maintained in place while being sufficiently forgiving such that the device 100 may be removed with minimal force.

Figure 14:
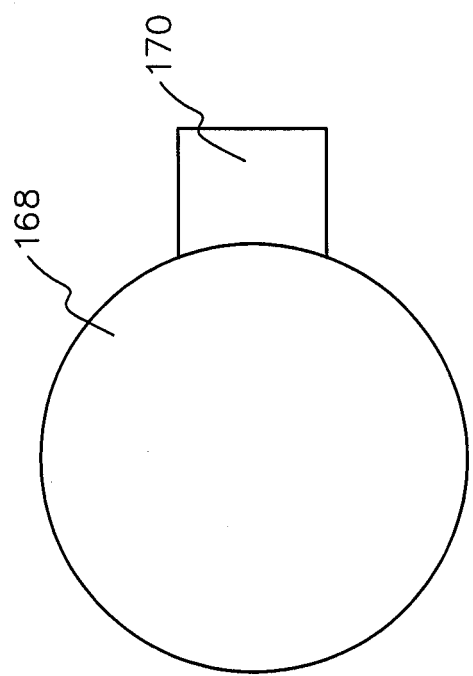
FIG. 14 is a top view of a human skull showing an outline of a cutout to receive a brain implant device and associated conduit.
Figure 15:
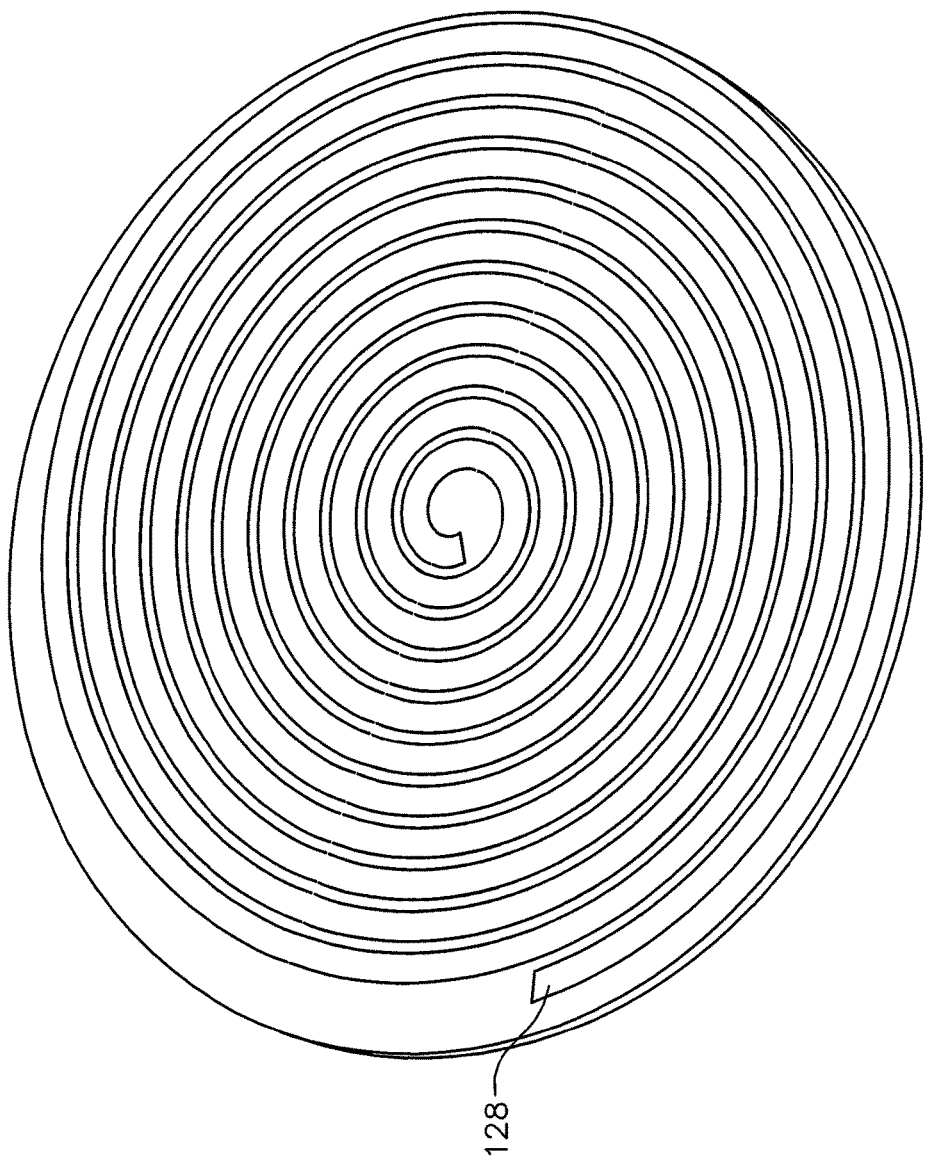
FIG. 15 is a schematic representation of a "helix" antenna.
Figure 16:
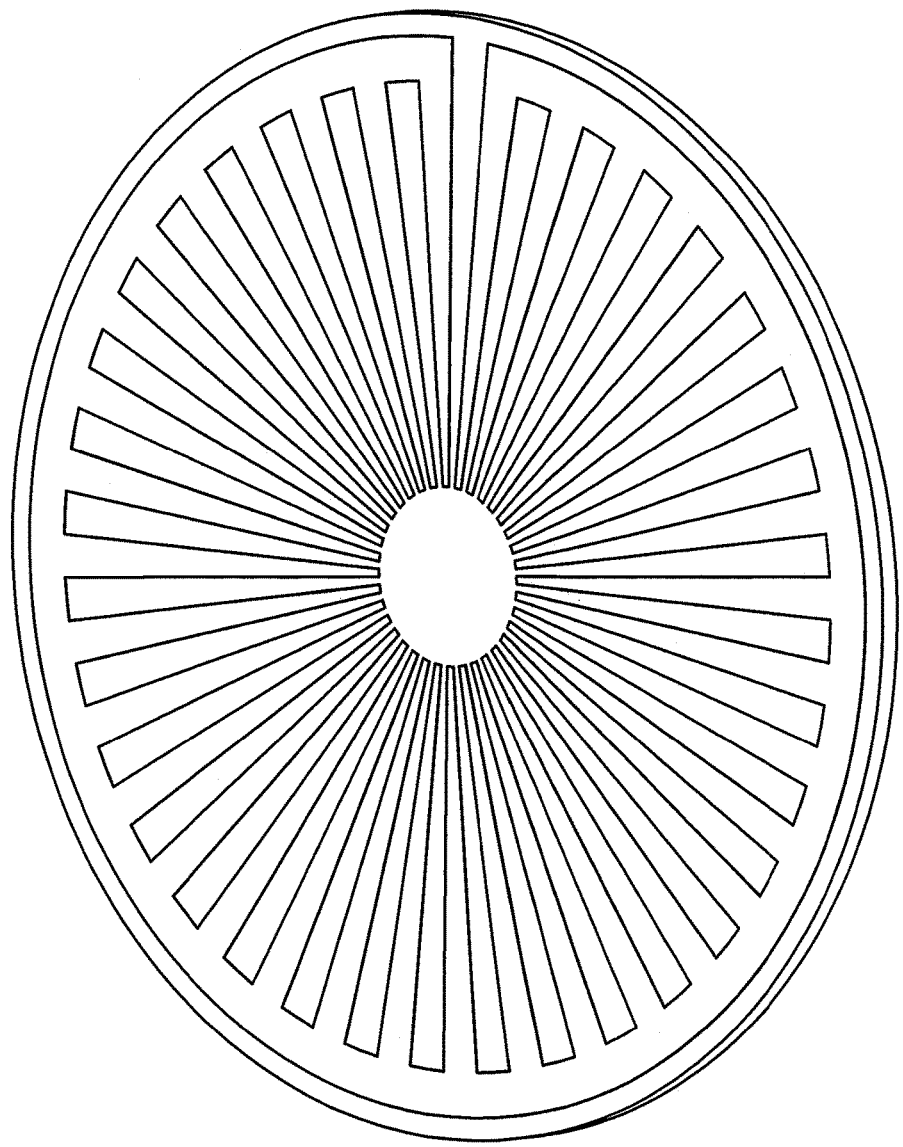
FIG. 16 is a schematic representation of a "starburst" antenna.
Figure 17:
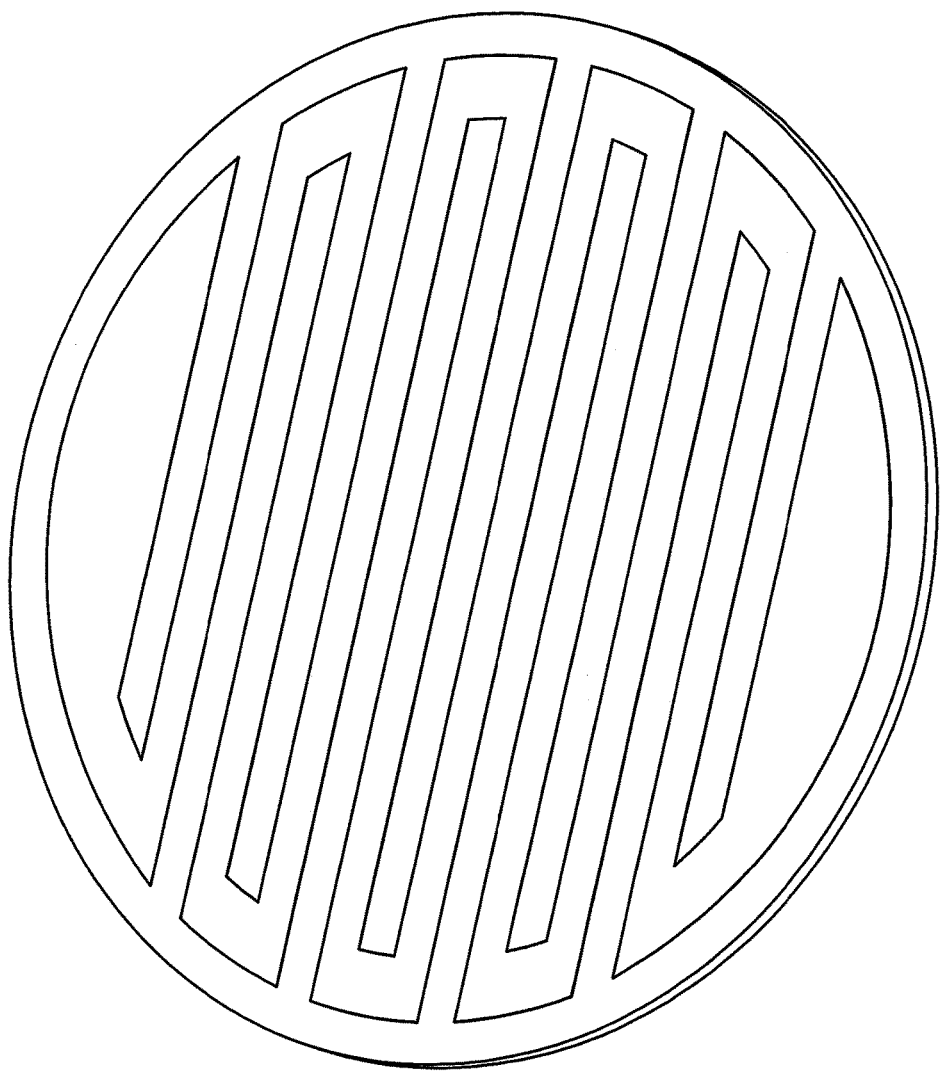
FIG. 17 is a schematic representation of a "zig-zag" antenna.

As an alternative insertion method, a square notch 170 (see FIG. 14) preferably in the order of 5 mm×5 mm may be "nibbled" into the skull immediately adjacent to the circular hole adapted to receive stem 104. The notch provides a passage way into which the electrode arrays may be inserted for placement in brain tissue. The circular hole and notch are located preferably in the close vicinity of selected brain tissue to be contacted for ease of location and placement of electrode arrays. The conduit 160 may be wedged partially within the notch to stabilize the conduit from moving once attached to selected brain tissue.

Although the present invention has been described with reference to multiple embodiments it is to be understood that still further embodiments are within the contemplation of the invention. As a mere example, antenna 128 may be any one of a number shapes including, but not limited to, the helix shown in FIG. 15, the "starburst" shown in FIG. 16, or the "zigzag" shown in FIG. 17.

What is claimed is:

1. A brain implant system comprising an implantable device, the implantable device comprising:
   a sealed housing;
   electronics contained within the housing and configured to receive and process signals from selected sites of a brain;
   an energy source contained within the housing and configured to provide energy to the electronics; and
   a flexible conduit in electrical communication with the electronics, said flexible conduit having a proximal end bonded together with said housing to form an integrally mounted unitary structure therewith, said flexible conduit extending from the housing and configured to contact brain tissue for communicating signals from selected sites of the brain to said electronics, wherein the electronics includes data processing circuitry configured to detect an attribute of the signals from selected sites of the brain according to at least one pre-selected criteria and to designate each occurrence of the detected attribute as a detected event, said data processing circuitry further configured to form a processed value corresponding to such detected events over a pre-selected interval of time.

2. The system of claim 1 further comprising an external communication device, wherein the electronics are adapted for wireless communication with the external communication device, said electronics further adapted to provide a measure of the signals from selected sites of the brain to the external communication device via a wireless communication link.

3. The system of claim 2 further comprising at least one implantable microdevice, wherein said external communication device comprises a master controller adapted to provide wireless communication between the implantable device and the at least one implantable microdevice.

4. The system of claim 3 wherein the at least one microdevice is configured to stimulate contraction of a muscle, and wherein the master controller commands the at least one microdevice to stimulate contraction of the muscle when the implantable device indicates that the signals from selected sites of the brain indicate an intention to contract the muscle.

5. The system of claim 4 wherein the at least one microdevice is configured to sense a depolarization signal emitted by the muscle, and wherein the master controller commands the implantable device to provide a signal to the brain when the microdevice senses the depolarization signal.

6. The system of claim 3 wherein the at least, one implantable microdevice is selected from the group consisting of: at least one microstimulator, at least one microsensor, and at least one combination microstimulator/microsensor.

7. The system of claim 1, wherein said signals from selected sites of the brain are sampled at a predefined rate and have a first data content measured in number of bits over the pre-selected interval of time and wherein said processed value has a second data content measured in number of bits over the pre-selected interval of time, said second data content having fewer bits than said first data content.

8. The system of claim 7, wherein said data processing circuitry is adapted to determine the average value of the number of detected events that exceed a first threshold value over the pre-selected time interval.

9. The system of claim 8, wherein said data processing circuitry is adapted to determine the average value of the number of detected events that exceed a second threshold value over the pre-selected time interval.

10. The system of claim 9, wherein the first threshold and second threshold define a window of eligible detected events for processing, said data processing circuitry adapted to determine an average number of detected events occurring within said window over a pre-determined time interval.

11. The system of claim 1, wherein the housing includes a plurality of feedthroughs and wherein the electronics comprises a plurality of individual channels, each channel adapted for processing signals related to selected brain sites, each channel electrically coupled to respective ones of the feedthroughs.

12. The system of claim 11, wherein the flexible conduit distal end comprises a plurality of electrically conductive protuberances, each protuberance having a tip portion, the tip portion being adapted for contact with a desired site on the brain, and wherein the flexible conduit proximal end comprises a plurality of electrical contacts adapted for electrical coupling to respective ones of the feedthroughs, and a conductor portion extending between the distal end and the proximal end, the conductor portion including a plurality of electrically conductive wires, each wire coupled between respective ones of the protuberances and the proximal end electrical contacts and adapted to convey signals between the protuberances and the proximal end.

13. The system of claim 12, wherein the conductive wires are selected from the group consisting of platinum, gold and copper and alloys thereof.

14. The system of claim 13, wherein the flexible conduit is configurable in a serpentine zig-zag fashion to provide contraction and extension thereof without dislodging the protuberances from brain sites.

15. The system of claim 11, wherein the energy source comprises a rechargeable battery and wherein each channel is electrically coupled to said battery to receive energy therefrom.

16. The system of claim 15, wherein the implantable device further comprises:
a coil disposed within the housing; and
charging circuitry coupled to the coil and the rechargeable battery, said charging circuitry configured to control delivery of energy to said rechargeable battery, said coil responsive to an external alternating magnetic field and adapted for supplying energy to said rechargeable battery via said charging circuitry.

17. The system of claim 16, wherein the implantable device further comprises a magnet positioned within the device and in proximity to the coil so as to concentrate the external alternating magnetic field for optimizing coupling between said magnetic field and the coil.

18. The system of claim 1 further comprising an implantable communication device, wherein the electronics are adapted for wireless communication with the implantable communication device, said electronics further adapted to provide a measure of the signals from selected sites of the brain to the implantable communication device via a wireless communication link.

19. The system of claim 18 further comprising at least one implantable microdevice, wherein the implantable communication device comprises a master controller adapted to provide wireless communication between the implantable device and at least one implantable microdevice.

20. The system of claim 19 wherein the at least one microdevice is configured to stimulate contraction of a muscle, and wherein the master controller commands the at least one microdevice to stimulate contraction of the muscle when the implantable device indicates that the signals from selected sites of the brain indicate an intention to contract the muscle.

21. The system of claim 20 wherein the at least one microdevice is configured to sense a depolarization signal emitted by the muscle, and wherein the master controller commands the implantable device to provide a signal to the brain when the microdevice senses the depolarization signal.

22. The system of claim 19 wherein the at least one implantable microdevice is selected from the group consisting of: at least one microstimulator, at least one microsensor, and at least one combination microstimulator/microsensor.

23. The system of claim 1 further comprising at least one implantable microdevice, wherein the electronics are adapted for wireless communication with the at least one implantable microdevice, said electronics further adapted to provide a measure of the signals from selected sites of the brain to the at least one microdevice via a wireless communication link.

24. The system of claim 23, wherein the at least one implantable microdevice comprises a plurality of implantable microdevices, and wherein the implantable device communicates with each one of the plurality of implantable microdevices via the wireless communication link.

25. The system of claim 23 wherein the at least one microdevice is configured to stimulate contraction of a muscle when the implantable device indicates that the signals from selected sites of the brain indicate an intention to contract the muscle.

26. The system of claim 25 wherein the at least one microdevice is configured to sense a depolarization signal emitted by the muscle, and wherein the implantable device provides a signal to the brain when the microdevice senses the depolarization signal.

27. The system of claim 23 wherein the at least one implantable microdevice is selected from the group consisting of: at least one microstimulator, at least one microsensor, and at least one combination microstimulator/microsensor.

28. The system of claim 1 wherein the selected sites of the brain comprise a motor cortex and a sensory cortex.

29. The system of claim 1 wherein the sealed housing is implantable below the interior surface of a skull housing the brain.

* * * * *